US00PP11215P

United States Patent [19]

VandenBerg

[11] Patent Number: Plant 11,215

[45] Date of Patent: Feb. 8, 2000

[54] CHRYSANTHEMUM PLANT NAMED 'NEW YOORLEANS'

[75] Inventor: Cornelis P. VandenBerg, Salinas, Calif.

[73] Assignee: Yoder Brothers, Inc., Barberton, Ohio

[21] Appl. No.: 09/113,137

[22] Filed: Jul. 9, 1998

[51] Int. Cl.[7] ..... A01H 5/00

[52] U.S. Cl. ..... Plt./286

[58] Field of Search ..... Plt./286, 297, 284

*Primary Examiner*—Howard J. Locker

*Attorney, Agent, or Firm*—C. A. Whealy

[57] ABSTRACT

A distinct cultivar of Chrysanthemum plant named 'New Yoorleans', characterized by its uniformly mounded plant habit; freely branching habit giving a full and dense appearance; uniform and early flowering; very floriferous, numerous inflorescences per plant; daisy spray-type inflorescences that are about 6.75 cm in diameter; unique red purple and white bi-colored ray florets with bright yellow disc florets; and good postproduction longevity with inflorescences and leaves maintaining good substance and color for about three or four weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name New Yoorleans. The plant is being marketed under the name New Orleans.

The new Chrysanthemum is a product of a planned breeding program conducted by the inventor in Salinas, Calif. The objective of the breeding program is to create new pot-type Chrysanthemum cultivars having desirable inflorescence forms and floret colors and excellent post-production longevity.

The new Chrysanthemum originated from a cross made by the breeder in May, 1993, in Salinas, Calif. of two unnamed proprietary Chrysanthemum seedling selections.

The new Chrysanthemum was discovered and selected by the inventor as a flowering plant within the progeny of the stated cross in a controlled environment in Salinas, Calif. in March, 1994. The selection of this plant was based on its desirable inflorescence form and floret colors and good post-production longevity.

Asexual reproduction of the new Chrysanthemum by terminal cuttings harvested in a controlled environment in Salinas, Calif., has shown that the unique features of this new Chrysanthemum are stable and reproduced true to type in successive generations.

SUMMARY OF THE INVENTION

The cultivar New Yoorleans has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'New Yoorleans'. These characteristics in combination distinguish 'New Yoorleans' as a new and distinct Chrysanthemum:

1. Uniformly mounded plant habit.
2. Freely branching habit, very full and dense.
3. Uniform and early flowering.
4. Very floriferous with numerous inflorescences per plant.
5. Daisy spray-type inflorescences that are about 6.75 cm in diameter.

6. Unique red purple and white bi-colored ray florets with bright yellow disc florets.
7. Good postproduction longevity with inflorescences and leaves maintaining good substance and color for about three or four weeks in an interior environment.

The new Chrysanthemum is similar in ray floret color to the commercial cultivar Tijuana (disclosed in U.S. Plant Pat. No. 9,083). However in side-by-side comparisons in Salinas, Calif., under commercial practice, plants of the new Chrysanthemum differed from plants of the cultivar Tijuana in the following characteristics:

1. Plants of the new Chrysanthemum are taller than plants of the cultivar Tijuana.
2. Plants of the new Chrysanthemum flower a few days later than plants of the cultivar Tijuana
3. Plants of the new Chrysanthemum have smaller inflorescences than plants of the cultivar Tijuana.
4. Ray florets of plants of the new Chrysanthemum have a more pronounced purple and white bi-colored pattern.
5. Plants of the new Chrysanthemum produce a small amount to no pollen whereas plants of the cultivar Tijuana produce abundant pollen.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a top perspective view of a typical flowering plant of 'New Yoorleans'.

The photograph at the bottom of the first sheet is a close-up view of typical inflorescences of plants of 'New Yoorleans'.

The photograph on the second sheet is a close-up view of upper and lower surfaces of typical inflorescences (top) and typical leaves (bottom) of plants of 'New Yoorleans'. Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used.

The following observations and measurements describe plants grown in Leamington, Ontario, Canada, and Salinas, Calif., under greenhouse conditions which approximate those generally used in commercial potted Chrysanthemum production. Four unrooted cuttings were directly stuck in a 15-cm container and pinched once. Measurements and numerical values represent averages of typical flowering plants.

Botanical classification: *Dendranthema grandiflora* cultivar New Yoorleans.

Commercial classification: Daisy spray-type pot chrysanthemum.

Parentage: Male or pollen parent: Unnamed proprietary *Dendranthema grandiflora* seedling selection. Female or seed parent: Unnamed proprietary *Dendranthema grandiflora* seedling selection.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous daisy spray-type pot Chrysanthemum. Inverted triangle. Stems initially upright, then somewhat spreading giving a uniformly mounded appearance to the plant. Very freely branching; about four or five lateral branches develop after removal of terminal apex (pinching), very dense and full plants.

*Plant height.*—About 27 cm.

*Plant width.*—About 35 cm.

*Foliage description.*—Arrangement: Alternate. Length: About 6.75 cm Width: About 5.75 cm. Apex: Mucronate. Base: Attenuate. Margin: Palmately lobed, sinuses between lateral lobes parallel. Texture: Upper and lower surfaces with very fine pubescence. Veins prominent on lower surface. Petiole length: About 1.75 cm Color: Young foliage upper surface: 147A. Young foliage lower surface: Close to 147B. Mature foliage upper surface: 147A. Mature foliage lower surface: Close to 147B. Venation upper surface: 147A. Venation lower surface: Close to 147B.

Inflorescence description:

*Appearance.*—Daisy spray-type inflorescence form with oblong-shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about eight weeks later.

*Postproduction longevity.*—Inflorescences and leaves will maintain good color and substance for about three or four weeks in an interior environment.

*Quantity of Inflorescences.*—Very floriferous; about ten inflorescences per terminal with about 45 inflorescences per plant.

*Inflorescence bud.*—Height: About 6 mm. Diameter: About 9 mm. Color: Close to 141A.

*Inflorescence size.*—Diameter: About 6.75 cm. Depth (height): About 1.4 cm Diameter of disc: About 1.7 cm.

*Ray florets.*—Shape: Oblong with short corolla tube. Aspect: Straight, mostly flat. Orientation: Upright. Length: About 3 cm. Width: About 1.1 cm. Apex: Acute. Margin: Entire. Texture: Smooth, glabrous. Number of ray florets per inflorescence: About 21. Color: When opening, upper surface: Apex, purple, close to 71A with white longitudinal streaks; base, white, 155D. When opening, lower surface: Apex, purple, close to 71A with white longitudinal streaks; base, white, 155D. Fully opened, upper surface: Mid-section and apex, purple, close to 71A to 61A to 64A with white longitudinal streaks; base, white, 155D. Fully opened, lower surface: Apex and margin, purple, close to 71A with white longitudinal streaks; base and mid-section, white, 155D.

*Disc florets.*—Shape: Tubular. Apex: Serrated. Length: About 6 mm. Width: Apex: About 2 mm. Base: About 1 mm. Number of disc florets per inflorescence: Numerous, about 93. Color: Immature: Greener than 154A. Mature: Apex: 9A. Mid-section: 154A/154C. Base: White, 155D.

*Peduncle.*—Aspect: Flexible, strong, angled about 45° to stem. Length, first peduncle: About 2.6 cm Length, fourth peduncle: About 4.7 cm. Texture: Pubescent. Color: Greener than 144A.

*Reproductive organs.*—Androecium: Present on disc florets only. Anther color: 13A. Pollen amount: Little to none observed. Gynoecium: Present on both ray and disc florets.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'New Yoorleans', as illustrated and described.

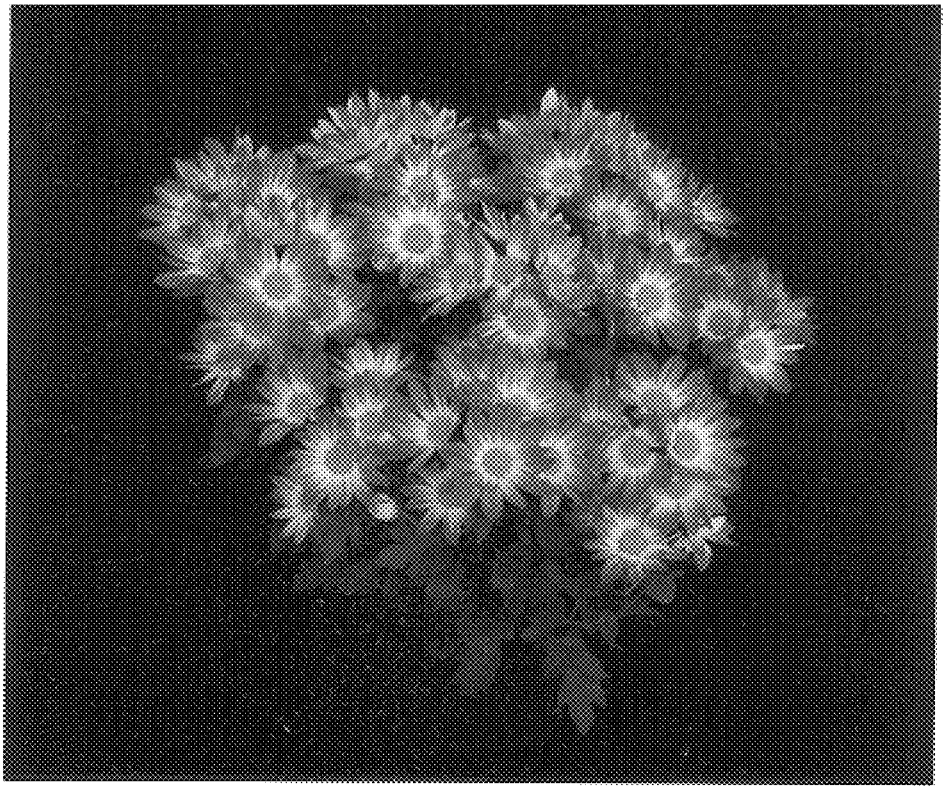
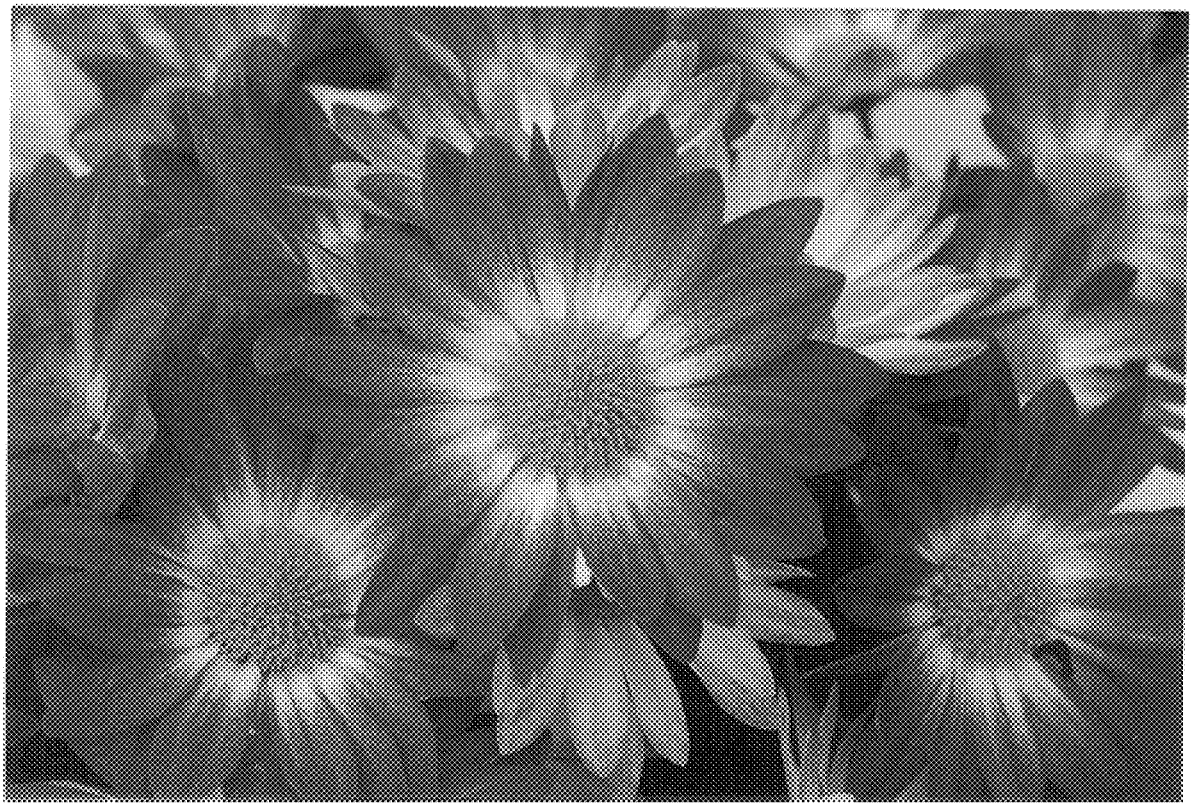

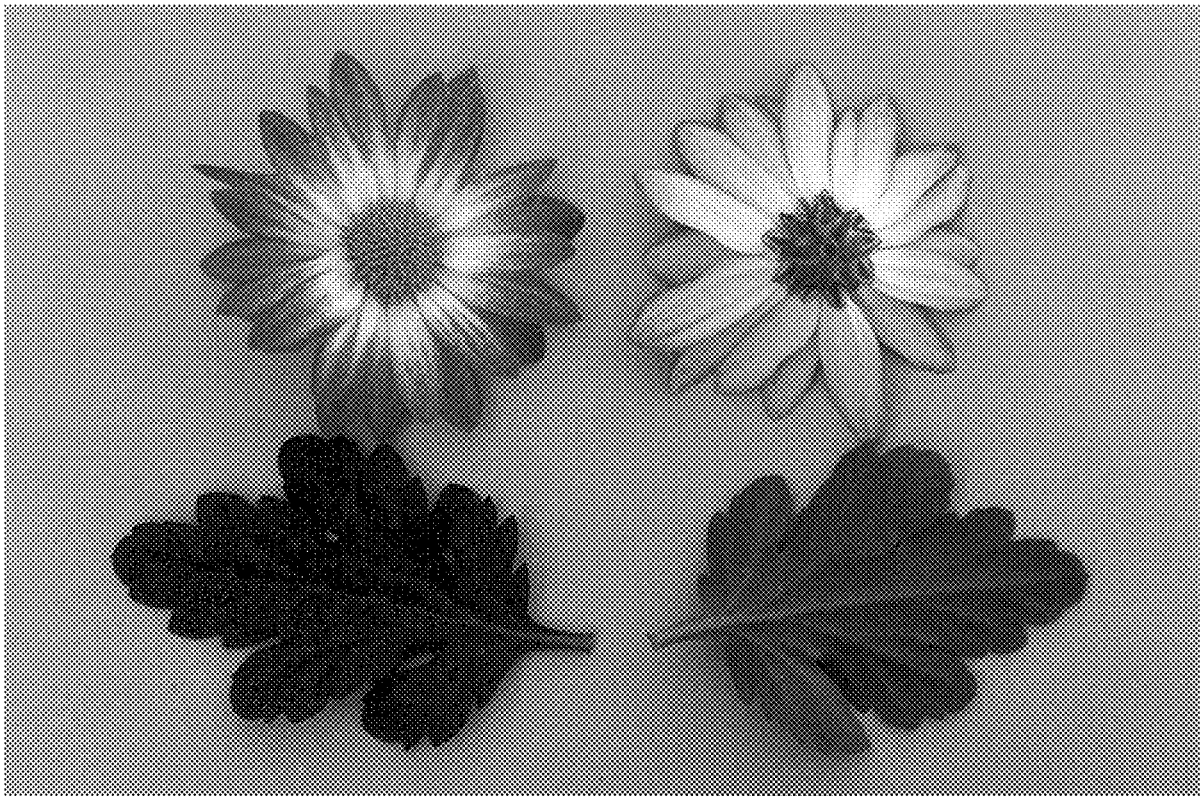

* * * * *